United States Patent
Levorse, Jr. et al.

(10) Patent No.: US 7,345,204 B2
(45) Date of Patent: Mar. 18, 2008

(54) SUBSTITUTED CYCLOPENTENONE DERIVATIVES AND THEIR USE IN PERFUME COMPOSITIONS

(75) Inventors: Anthony T. Levorse, Jr., Westfield, NJ (US); Richard A. Weiss, Livingston, NJ (US); Brett D. Newirth, Atlantic Highlands, NJ (US)

(73) Assignee: International Flavors & Fragrances Inc, New York, NY (US)

( * ) Notice: Subject to any disclaimer, the term of this patent is extended or adjusted under 35 U.S.C. 154(b) by 65 days.

(21) Appl. No.: 11/419,874

(22) Filed: May 23, 2006

(65) Prior Publication Data

US 2007/0004608 A1    Jan. 4, 2007

Related U.S. Application Data

(63) Continuation-in-part of application No. 11/173,539, filed on Jul. 1, 2005, now Pat. No. 7,141,699.

(51) Int. Cl.
  *C07C 49/537*    (2006.01)
  *A61K 7/46*    (2006.01)

(52) U.S. Cl. ............................ 568/379; 512/9; 512/27
(58) Field of Classification Search ...................... None
  See application file for complete search history.

(56) References Cited

OTHER PUBLICATIONS

Harrington-Frost et al. Novel Intramolecular Cyclisations Involving Ketene Radical Intermediates as an Approach to the Synthesis of Polyquinanes. Synlett, 1999, No. 12, pp. 1917-1918.*
Matlin et al. Regiochemical Control in Intramolecular Photochemical Reactions of 1,6-Heptadienes: Carbonyl-Substituted 1-(4-Alkenyl)-1-cyclopentenes. Journal of the American Chemical Society, 1986, vol. 108, pp. 3385-3394.*

* cited by examiner

*Primary Examiner*—Sikarl A. Witherspoon
(74) *Attorney, Agent, or Firm*—Elizabeth M. Quirk; XuFan Tseng; Joseph F. Leightner

(57) ABSTRACT

The present invention relates to substituted cyclopentanone derivatives and their use as fragrance chemicals suitable for incorporation in fine fragrances, cosmetics, toiletries and related applications.

8 Claims, No Drawings

SUBSTITUTED CYCLOPENTENONE DERIVATIVES AND THEIR USE IN PERFUME COMPOSITIONS

STATUS OF RELATED APPLICATIONS

This application is a continuation in part of U.S. Ser. No. 11/173,539, filed on Jul. 1, 2005, now U.S. Pat. No. 7,141,699 the contents hereby incorporated by reference as if set forth in its entirety.

FIELD OF THE INVENTION

The present invention relates to new substituted cyclopentenone derivatives and their use as fragrance chemicals suitable for incorporation in fine fragrances, cosmetics, toiletries and related applications.

BACKGROUND OF THE INVENTION

There is an ongoing need in the fragrance industry to provide new chemicals to give perfumers and other people the ability to create new fragrances for perfumes, colognes and personal care products. Those with skill in the art appreciate how differences in the chemical structure of the molecule can result in significant differences in the odor, notes and characteristics of a molecule. These variations and the ongoing need to discover and use the new chemicals in the development of new fragrances allow perfumers to apply the new compounds in creating new fragrances.

SUMMARY OF THE INVENTION

The present invention provides novel chemicals, and the use of the chemicals to enhance the fragrance of perfumes, toilet waters, colognes, personal products and the like. More specifically, the present invention is directed to substituted cyclopentenone derivatives compounds represented by the general structure of Formula I set forth below:

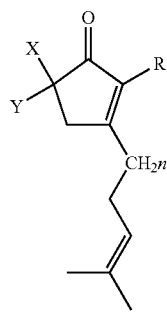

Formula I wherein R is selected from the group consisting of H, CH3 and CH2-CH3; X and Y is independently selected from H, CH3 and CH2-CH3; and n is an integer equal to 0, 1 or 2.

In a further embodiment of the invention a composition is provided comprising a compound with the formula

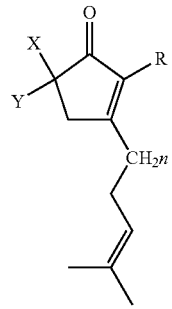

Formula I wherein R is selected from the group consisting of H, $CH_3$ and $CH_2$-$CH_3$; X and Y are selected from the group consisting of H, $CH_3$ and $CH_2$-$CH_3$; n is an integer equal to 0, 1 or 2; and 3-methyl-2-(3-methyl-2-butenyl)-2-cyclopenten-1-one.

Another embodiment of the present invention provides a composition comprising 3-(4-methyl-3-pentenyl)-2-cyclopenten-1-one and 3-methyl-2-(3-methyl-2-butenyl)-2-cyclopenten-1-one.

In yet another embodiment a method is disclosed for enhancing a perfume by incorporating an olfactory acceptable amount of the compounds provided above.

These and other embodiments of the present invention will be apparent by reading the following specification.

DETAILED DESCRIPTION OF THE INVENTION

In one embodiment of the invention, a composition is provided comprising Formula I and 3-methyl-2-(3-methyl-2-butenyl)-2-cyclopenten-1-one is provided.

In a further embodiment of the present invention a novel compound is disclosed represented by Structure I:

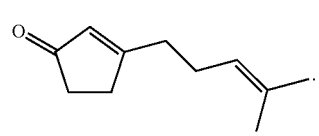

Structure I

Those with the skill in the art will appreciate that the compound of Structure I is 3-(4-methyl-3-pentenyl)-2-cyclopenten-1-one.

The novel structure of Structure I imparts unexpected organoleptic properties. Structure I has an intense dry bergamot, nerol odor and an intense fresh citrus, floral and fruity odor.

The odor properties of Structure I are all the more surprising when compared with 2-methyl-3-(3-methyl-2-butenyl)-2-cyclopenten-1-one, disclosed in Weyerstahl et al.(Flavour and Fragrance Journal 1996. 2-methyl-3-(3-methyl-2-butenyl)-2-cyclopenten-1-one and described as having a typical jasmone odor, slightly cumin and celery.

The odor differences between the two molecules are a result of the differences in both the molecular weight of the molecules and in their spatial orientation. The comparison of Structure I and Structure II below illustrates the structural differences of these compounds.

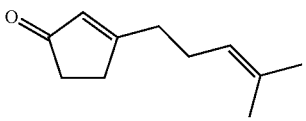

Structure I:

3-(4-methyl-3-pentenyl)-2-cyclopenten-1-one possesses intense dry bergamot, nerol odor and an intense fresh citrus, floral and fruity odor.

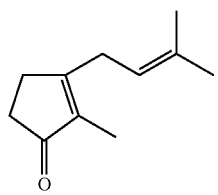

Structure II:

2-methyl-3-(3-methyl-2-butenyl)-2-cyclopenten-1-one disclosed in Weyerstahl et al. and described as having a typical jasmone odor, slightly cumin and celery.

Accordingly in a further embodiment a composition comprising 3-(4-methyl-3-pentenyl)-2-cyclopenten-1-one and 3-methyl-2-(3-methyl-2-butenyl)-2-cyclopenten-1-one is provided.

According to the present invention 3-methyl-2-(3-methyl-2-butenyl)-2-cyclopenten-1-one can be represented by the following structure:

Structure III

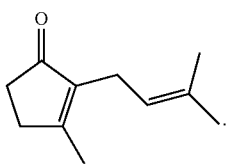

In an additional embodiment of the present invention a composition is provided comprising from about 20% to about 80% 3-(4-methyl-3-pentenyl)-2-cyclopenten-1-one and from about 80% to about 20% 3-methyl-2-(3-methyl-2-butenyl)-2-cyclopenten-1-one.

We have discovered that the composition comprising 3-(4-methyl-3-pentenyl)-2-cyclopenten-1-one and 3-methyl-2-(3-methyl-2-butenyl)-2-cyclopenten-1-one has citrus floral odor.

The compounds of the present invention may be prepared from the corresponding protected 1,3-cyclopentadione and cyclopentadienone, via Grignard reaction and alkylation reaction respectively.

As described in the examples below, compound of the Formulae I maybe prepared via standard ketone Grignard chemistry. A mono protected 1,3-cyclopentadione is treated with a freshly prepared magnesium Grignard of 1-Bromo-4-methyl-3-pentene which after workup affords structure I.

Structure II maybe prepared via base condensation chemistry between 3-methyl-2-cyclopentenone and prenyl chloride with phase transfer catalysis. The literature procedure of Mann and Armstead (Syn. Comm. 15(13), 1147 (1985)) was employed as a reference to prepare 3-methyl-2-(3-methyl-2-butenyl)-2-cyclopenten-1-one. The chemical yields were similar to those reported.

The composition comprising 3-(4-methyl-3-pentenyl)-2-cyclopenten-1-one and 3-methyl-2-(3-methyl-2-butenyl)-2-cyclopenten-1-one can be prepared by combining each of the compounds to form the composition.

The starting materials and reagents are available from Aldrich Chemical Company.

The synthesis of these compounds is described in the examples below.

The use of this compound is widely applicable in current perfumery products, including the preparation of perfumes and colognes, the perfuming of personal care products such as soaps, shower gels, and hair care products as well as air fresheners, candles and cosmetic products. The compound can also be used to perfume candles and cleaning agents, such as, but not limited to soaps, detergents, dishwashing materials, scrubbing compositions, window cleaners, fabric care products such as but not limited to fabric softeners, dryer sheets and the like.

In these preparations, the compound of the present invention can be used alone or in combination with other fragrance compositions, solvents, adjuvants and the like. Those with skill in the art will appreciate the nature and variety of the other ingredients that can be used in combination with the compound of the present invention.

Many types of fragrances can be employed in the present invention, the only limitation being the compatibility with the other components being employed. Suitable fragrances include but are not limited to fruits such as almond, apple, cherry, grape, pear, pineapple, orange, strawberry, raspberry, musk, flower scents such as lavender-like, rose-like, iris-like, and carnation-like. Other pleasant scents include herbal and woodland scents derived from pine, spruce and other forest smells. Fragrances may also be derived from various oils, such as essential oils, or from plant materials such as peppermint, spearmint and the like.

A list of suitable fragrances is provided in U.S. Pat. No. 4,534,891, the contents of which are incorporated by reference as if set forth in its entirety. Another source of suitable fragrances is found in *Perfumes, Cosmetics and Soaps*, Second Edition, edited by W. A. Poucher, 1959. Among the fragrances provided in this treatise are acacia, cassie, chypre, cyclamen, fern, gardenia, hawthorn, heliotrope, honeysuckle, hyacinth, jasmine, lilac, lily, magnolia, mimosa, narcissus, freshly-cut hay, orange blossom, orchid, reseda, sweet pea, trefle, tuberose, vanilla, violet, wallflower, and the like.

As used herein olfactory effective amount is understood to mean the amount of compound in perfume compositions the individual component will contribute to its particular olfactory characteristics, but the olfactory effect of the perfume composition will be the sum of the effects of each of the perfume or fragrance ingredients. Thus the compounds of the invention can be used to alter the aroma characteristics of the perfume composition by modifying the olfactory reaction contributed by another ingredient in the composition. The amount will vary depending on many factors including other ingredients, their relative amounts and the effect that is desired.

The level of compound of the invention employed in the perfumed article varies from about 0.005 to about 10 weight percent, preferably from about 0.1 to about 8 and most preferably from about 0.5 to about 5 weight percent. In addition to the compounds, other agents can be used in conjunction with the fragrance. Well known materials such as surfactants, emulsifiers, and polymers to encapsulate the fragrance can also be employed without departing from the scope of the present invention.

Another method of reporting the level of the compound of the invention in the perfumed composition, i.e., the compounds as a weight percentage of the materials added to impart the desired fragrance. The compounds of the invention can range widely from 0.005 to about 10 weight percent of the perfumed composition, and preferably from about 0.1 to about 5 weight percent. Those with skill in the art will be able to employ the desired level of the compound of the invention to provide the desired fragrance and intensity.

All U.S. Patents and patent applications cited herein are incorporated by reference as if set forth herein in their entirety.

The following are provided as specific embodiments of the present invention. Other modifications of this invention will be readily apparent to those skilled in the art, without departing from the scope of this invention. Upon review of the foregoing, numerous adaptations, modifications and alterations will occur to the reviewer. These adaptations, modifications, and alterations will all be within the spirit of the invention. Accordingly, reference should be made to the appended claims in order to ascertain the scope of the present invention.

As used herein all percentages are weight percent. IFF is meant to be understood as International Flavors & Fragrances Inc.

EXAMPLE 1

Preparation of
3-(4-methyl-3-pentenyl)-2-cyclopenten-1-one:

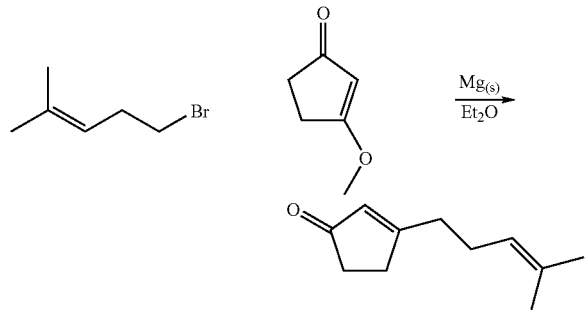

Magnesium turnings 2.1 g (0.086 mole) were added to 50 ml diethyl ether with stirring. 1-Bromo-4-methyl-3-pentene 10 g (0.061 mole) was added dropwise over 30 minutes. The reaction was allowed to warm from 25° C. to 40° C. during the addition and aged for 30 minutes. A solution of 3-Methoxy-2-cyclopenten-1-one, 10 g (0.089 mole) in diethyl ether was added at 25° C. The resulting mixture was aged 30 minutes then quenched with 20% aqueous acetic acid (50 ml). The organic layer was dried over sodium sulfate, filtered and distilled to give 6.6 g (65% yield) of 3-(4-methyl-3-pentenyl)-2-cyclopenten-1-one.

3-(4-methyl-3-pentenyl)-2-cyclopenten-1-one was evaluated and had the following fragrance evaluation.

| Dry | Intensity | Fresh |
|---|---|---|
| Bergamet, Nerol | 3 | Citrus, Floral, Fruity |
| | 2 | |
| | 1 | |

The 3-(4-methyl-3-pentenyl)-2-cyclopenten-1-one had a boiling point (Bp) of 117° C. at 5 mmHg.

NMR data: 1.62 ppm (s, 3H), 1.69 ppm (s, 3H), 2.28 ppm (q, 2H, J=7.21 Hz), 2.39-2.41 ppm (m, 2H), 2.44 ppm (t, 2H, J=7.46 Hz), 2.58 ppm (m, 2H), 5.09 ppm (t, 1H, J=6.69 Hz), 5.96 ppm (s, 1H).

EXAMPLE 2

Preparation of 3-methyl-2-(3-methyl-2-butenyl)-2-cyclopenten-1-one:

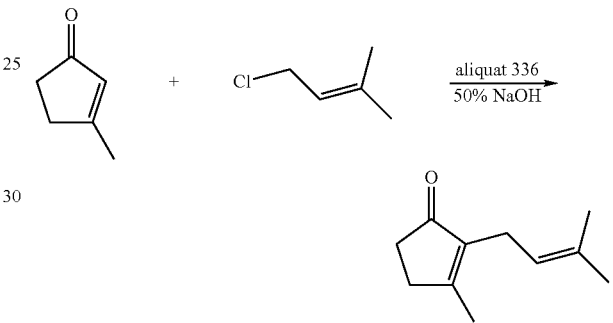

A mixture of 3-methyl-2-cyclopentenone 24.5 g (0.25 mole) and prenyl chloride 54 g (0.51 mole) was fed into a reaction flask containing 30 ml of toluene, sodium hydroxide 21.3 g, water 21.3 g and Aliquat 336 1 g maintaining 100° C. The reaction mass was aged for 4 hours, cooled to 25° C. and neutralized with acetic acid. The organic layer was removed and distilled to give 20.5 g of 3-methyl-2-(3-methyl-2-butenyl)-2-cyclopenten-1-one.

The 3-methyl-2-(3-methyl-2-butenyl)-2-cyclopenten-1-one had a Bp of 115° C. at 5 mmHg.

NMR data: 1.65 ppm (s, 3H), 1.69 ppm (s, 3H), 2.04 ppm (s, 3H), 2.35 ppm (m, 2H), 2.47 ppm (m, 2H), 2.86 ppm (d, 2H, J=7 Hz), 5.02 ppm (m, 1H). The data are in agreement with the literature reference of Mann and Armstead (Syn. Comm. 15(13), 1147 (1985).

What is claimed is:

1. A method of improving, enhancing or modifying a fragrance formulation through the addition of an olfactory acceptable amount of 3-(4-methyl-3-pentenyl)-2-cyclopenten-1-one.

2. The method of claim 1, wherein the fragrance formulation is incorporated into a product selected from the group consisting of a perfume, a cologne, a toilet water, a cosmetic product, a personal care product, a fabric care product, a cleaning product and an air freshener.

3. The method of claim 2, wherein the cleaning product is selected from the group consisting of detergents, dishwashing compositions, scrubbing compounds and window cleaners a detergent, a dishwashing composition, a scrubbing compound and a window cleaner.

4. The method of claim 1, wherein the amount added into the fragrance formulation is from about 0.005 to about 10 weight percent.

5. The method of claim 1, wherein the amount added into the fragrance formulation is from about 0.5 to about 8 weight percent.

6. The method of claim 1, wherein the amount added into the fragrance formulation is from about 1 to about 7 weight percent.

7. A fragrance formulation containing an olfactory effective amount of 3-(4-methyl-3-pentenyl)-2-cyclopenten-1-one.

8. A fragrance product containing 3-(4-methyl-3-pentenyl)-2-cyclopenten-1-one.

\* \* \* \* \*